US005661170A

United States Patent [19]

Chodosh

[11] Patent Number: 5,661,170
[45] Date of Patent: Aug. 26, 1997

[54] ANTIMICROBIAL COMPOSITIONS AND METHODS FOR USING THE SAME

[75] Inventor: Daniel Frank Chodosh, Meadowbrook, Pa.

[73] Assignee: Woodward Laboratories, Inc., Los Alamitos, Calif.

[21] Appl. No.: 662,906

[22] Filed: Jun. 12, 1996

Related U.S. Application Data

[60] Continuation of Ser. No. 458,406, Jun. 2, 1995, abandoned, which is a division of Ser. No. 215,365, Mar. 21, 1994, abandoned.

[51] Int. Cl.$^6$ .................................................. A61K 6/00
[52] U.S. Cl. .......................... 514/390; 514/383; 514/384; 514/599; 514/642; 514/643; 514/975; 514/882; 514/887; 514/901; 514/944; 514/966; 514/967; 424/54
[58] Field of Search .................................. 514/390, 599, 514/975, 642, 643, 383, 384; 424/54

[56] References Cited

U.S. PATENT DOCUMENTS

| | | | |
|---|---|---|---|
| 2,577,773 | 3/1951 | Lambert | 252/152 |
| 3,419,006 | 12/1968 | King | 128/268 |
| 3,968,246 | 7/1976 | Merianos et al. | 424/330 |
| 4,203,872 | 5/1980 | Flanagan | 252/542 |
| 4,278,664 | 7/1981 | Van Cleave | 424/148 |
| 4,336,151 | 6/1982 | Like et al. | 252/106 |
| 4,797,420 | 1/1989 | Bryant | 514/643 |
| 5,181,914 | 1/1993 | Zook | 604/307 |
| 5,284,833 | 2/1994 | McAnalley et al. | 514/23 |
| 5,362,422 | 11/1994 | Masters | 252/544 |
| 5,439,682 | 8/1995 | Wivell et al. | 424/401 |

FOREIGN PATENT DOCUMENTS 2108840 5/1983 United Kingdom.

OTHER PUBLICATIONS

Fisher, Alexander A., M.D., "Allantoin: A Non–Sensitizing Topical Medicament Therapeutic Effects of the Addition of 5 Percent Allantoin to Vaseline®", 1981, pp. 1–3.

Katz, Nadya Dimitrov, D.P.M., "Tough as Nails . . . Fungoid® Tincture", Cutis, May, 1992.

Sutton Laboratories, Inc., Fact Sheet on Allantoin, Jan. 1, 1992, pp. 1–6.

Allantoin Product Information, published by Sutton Laboratories, Inc.

Germaben® II–E Product Information, published by Sutton Laboratories, Inc.

Nadya Dimitrov Katz, D.P.M., Tough As Nails . . . Fungold® Tincture, Cutis, May, 1992.

*Primary Examiner*—Frederick Krass
*Attorney, Agent, or Firm*—Woodcock Washburn Kurtz Mackiewicz & Norris LLP

[57] ABSTRACT

Antimicrobial compositions useful in the treatment of microbial infections and as general cleansers are provided along with methods for their administration. The antimicrobial compositions are aqueous based and preferably contain a quaternary ammonium compound as a antimicrobial agent. The antimicrobial compositions also preferably contain a surfactant such as a cationic, nonionic, or amphoteric surfactant or mixtures thereof. A keratolytic agent, such as allantoin, is also preferably blended into the antimicrobial compositions. The antimicrobial compositions are ideally suited for subcutaneous, cutaneous, or mucosal membrane administration.

42 Claims, 1 Drawing Sheet

ANTIMICROBIAL COMPOSITIONS AND METHODS FOR USING THE SAME

This is a continuation of application Ser. No. 08/458,406, filed Jun. 2, 1995, now abandoned which is a divisional of U.S. Ser. No. 08/215,365, filed Mar. 21, 1994, now abandoned.

FIELD OF THE INVENTION

This invention relates to antimicrobial compositions useful in the treatment of microbial infections. In particular, the compositions are advantageous for topical application to humans, especially to nails and adjacent tissue for the treatment of mycotic and bacterial infections.

BACKGROUND OF THE INVENTION

Fungal infections of nails, both toe nails and finger nails, are a widespread problem, especially to people with compromised peripheral circulation such as the elderly, chronically ill, and diabetic. Others afflicted with such infections include workers in the medical field, farmers, persons with military service backgrounds, and users of acrylic nail care products. These infections are irritating and are not easily eliminated, even with repeated applications of commonly prescribed treatments.

Biologically active antimicrobial compounds have proved difficult to administer by the topical route for the treatment of mycotic (yeast, mold, and fungal) and bacterial infections of human nails and adjacent tissue. Commonly applied topical formulations such as creams, ointments, tinctures, aqueous and non-aqueous solutions and suspensions and the like are typically absorbed or rubbed off onto socks and shoes when applied to the toenails and adjacent tissue; likewise, formulations applied topically to the fingernails and adjacent tissue are typically absorbed onto clothing or gloves or rubbed off incidently during hand washing. Moreover, it has not been adequately demonstrated that the previously used topical formulations deliver therapeutically adequate doses of the biologically active antimicrobial material to the mycotic or bacterially infected tissue when applied to the nail and adjacent tissue.

Various attempts have been made to address the inadequacies of the topical administration of the antimicrobial compositions including the development of various medicating devices for the human nails and adjacent tissues. An example of such a device is set forth in U.S. Pat. No. 5,181,914 which discloses a device which occlusively covers the targeted tissue area with a bandage type device having a medication reservoir. The therapeutic efficacy of such devices markedly depends on the specific biologically active compound employed and the ability of the applied formulation to effectively deliver the active compound to the affected tissue. Furthermore, such treatment requires that the patient wear such a device throughout the treatment.

Research relating to the treatment of infections has primarily centered around the compositions used for treating the infected tissue areas. Various compositions have been developed and used by the medical industry. For example, a composition containing the water insoluble fungistatic agent undecylenic acid with the topical antiseptic agent chloroxylenol in an oil based solvent has been sold under the trade name GORDOCHOM (Gordon Laboratories, Upper Darby, Pa.). Also, a composition containing the fungistatic agent triacetin, topical antiseptic agents chloroxylenol and cetyl pyridinium chloride, alcohols, and a keratolytic agent glacial acetic acid in an aqueous tincture with several cosmetic preservatives has been sold under the name Fungoid® Tincture (PEDiNOL Pharmacal, Farmingdale N.Y.). The Fungoid® composition has also been formulated using the fungicidal agent miconazol nitrate. Further, a composition sold under the trade name FungiNail® (Kramer Laboratories, Fla.) containing a fungistatic agent undecylenic acid with a topical antiseptic agent chloroxylenol and several keratolytic agents such as acetic acid and salicylic acid in a vehicle containing alcohol and a topical anethestic agent benzocaine. Finally a further composition sold under the name Moné (Kenlor Industries, Santa Aria Calif.) containing an antimicrobial agent didecyl dioctyl ammonium chloride with several surfactants and several cosmetic preservatives in an aqueous media has also been used for the treatment of microbial infections. Several of the prior compositions contain acids, alcohols and other non-aqueous solvents which have been demonstrated to cause contact dermatitis if topical administration is chronic or in sufficiently high concentration. Further, several of the compositions containing active agents other than the quaternary ammonium compounds may be ineffective in delivering the active agent to the human nails and adjacent tissue and are thus of unproven therapeutic value.

A need therefore exists to develop an antimicrobial composition which can deliver the antimicrobial agent effectively to the site of the infection, such as an infected nail and surrounding tissue area. The antimicrobial compositions should therefore not only contain an effective antimicrobial agent but also be in a form that can effectively deliver that active agent to the infected area when administered topically.

SUMMARY OF THE INVENTION

Antimicrobial compositions are set forth which contain a biologically effective, therapeutic, non-toxic quantity of an antimicrobial agent in admixture with either a nonionic, cationic, or amphoteric surfactant, or mixture of such surfactants. The preferred antimicrobial agents are quaternary ammonium compounds, especially benzalkonium chloride, present in an amount of from about 0.05–5 weight percent of the antimicrobial composition. Various other antimicrobial agents can be used in combination with or as a replacement for, the quaternary ammonium compounds.

The antimicrobial compositions preferably also contain a keratolytic agent such as allantoin. The presence of the allantoin increases the effectiveness of the antimicrobial compositions. The allantoin or other keratolytic agent is present in the antimicrobial compositions in an amount of from about 0.05–5 weight percent.

The antimicrobial compositions are useful in reducing the extent of a microbial infection on the body of an animal, such as a human. The compositions are administered either cutaneously or subcutaneously or to the mucous membranes. The administration is preferably to the skin, hair, or nails and surrounding tissue of an animal. The compositions can also be applied to the hooves, claws, and beaks of animals. The preferred application of the compositions is for the treatment of mycotic and bacterially infected human nails and adjacent tissue, especially for the treatment of onychomycosis, onychia, and paronychia.

The antimicrobial compositions can also be used as cleansing compositions for treating the skin of an animal. Further, the compositions can be used in a prophylactic manner for administration to the skin of an animal.

DETAILED DESCRIPTION OF THE INVENTION

Figure 1:
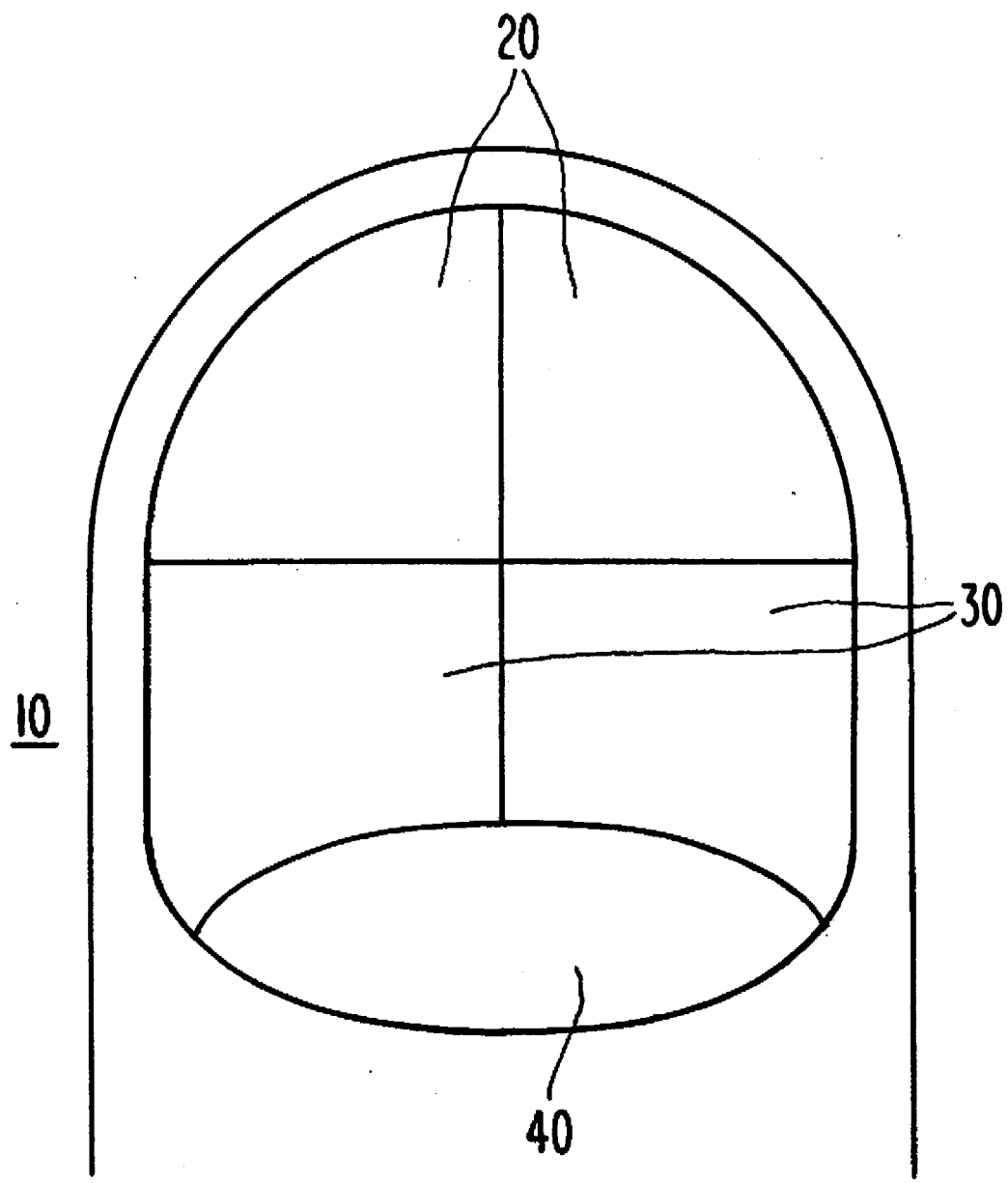
FIG. 1 is a depiction of a human nail divided into five sections, which was used as a quantitative testing basis for the Example.

The present invention provides antimicrobial pharmaceutical compositions and methods for their application to cutaneous and subcutaneous tissue and also mucous membrane tissues. The present invention also provides methods of preparing the antimicrobial pharmaceutical compositions. The antimicrobial compositions contain a biologically active antimicrobial agent or mixtures thereof and a surfactant or mixture thereof. The antimicrobial agent is present in the antimicrobial composition in a biologically effective, therapeutic, non-toxic concentration. Preferably, a keratolytic agent or mixture thereof can be present in the compositions. Unless explicity started otherwise, all weight percentages in the specification and claims are based on the total weight of the antimicrobail composition.

The antimicrobial agents present in the antimicrobial compositions are preferably quaternary ammonium compounds, for example, benzalkonium chloride, benzethonium chloride, methylbenzethonium chloride, and didecyldioctyl ammonium chloride, more preferably benzalkonium chloride. The concentration of the quaternary ammonium compound present in the antimicrobial compositions ranges from about 0.05–5, preferably from about 0.1–2.5, and more preferably from about 0.13–2, weight percent.

Other antimicrobial agents can be used instead of, or in conjunction with, the quaternary ammonium compounds. These medicaments include one or more of the groups of compounds known as imidazoles (such as miconazole, ketoconazole, clotrimazole, econazole, oxiconazole, and isoconazole, and nitrates thereof), triazoles (such as fluconazole), and other compounds such as tolnaftate, naftifine hydrochloride, terbinafine hydrochloride, ciclopirox olamine, and haloprogin. Table 1 sets forth various preferred antimicrobial agents and ranges for their incorporation into the compositions.

TABLE 1

| Component | Broad | Preferred | Optimal |
| --- | --- | --- | --- |
| miconazole 1-[2-(2,4-dichlorophenyl)-2-[(2,4-dichlorophenyl)methoxy]ethyl]-1H-imidazole | 0.5–5.0 | 1.0–3.0 | 1.5–2.5 |
| miconazole nitrate 1-[2,4-dichloro-β-{(2,4-dichlorobenzyl)-oxy}phenethyl] imidazole mononitrate | 0.5–5.0 | 1.0–3.0 | 1.5–2.5 |
| ketoconazole cis-1-acetyl-4-[4-[[2-(2,4-dichlorophenyl)-2-(1H-imidazol-1-ylmethyl)-1,3-dioxolan-4-yl]methoxy]-phenyl]piperazine | 0.5–5.0 | 1.0–3.0 | 1.5–2.5 |
| clotrimazole 1-(o-chloro-α-α-diphenylbenzyl)imidazole | 0.25–4.0 | 0.5–1.5 | 0.75–1.25 |
| econoazole nitrate 1-[2-{(4-chlorophenyl)methoxy}-2-(2,4-dichlorophenyl)ethyl]-1H-imidazole mononitrate | 0.25–4.0 | 0.5–1.5 | 0.75–1.25 |
| oxiconazole nitrate 2',4'-dichloro-2-imidazol-1-ylacetophenone(Z)-[o-(2,4-dichlorobenzyl)oxime] mononitrate | 0.25–4.0 | 0.5–1.5 | 0.75–1.25 |
| isoconazole nitrate 1-[2,4-dichloro-b-(2,6-dichlorobenzyloxy)phenethyl] imidazole nitrate | 0.25–4.0 | 0.5–1.5 | 0.75–1.25 |
| fluconazole 2,4-difluoro-α,α$_1$-bis(1H-1,2,4-triazol-1-ylmethyl)benzyl alcohol | 0.25–4.0 | 0.5–1.5 | 0.75–1.25 |
| tolnaftate O-2-naphthyl N,N-dimethylthiocarbanilate | 0.25–4.0 | 0.5–1.5 | 0.75–1.25 |
| naftifine hydrochloride (E)-N-cinnamyl-N-methyl-1-naphthalenemethylamine hydrochloride | 0.25–4.0 | 0.5–1.5 | 0.75–1.25 |
| terbinafine hydrochloride (E)-N-(6,6-dimethyl-1-naphthalenemethanamine hydrochloride | 0.25–4.0 | 0.5–1.5 | 0.75–1.25 |
| ciclopirox olamine 6-cyclohexyl-1-hydroxy-4-methyl-2(1H)-pyridone, 2-aminoethanol salt | 0.25–4.0 | 0.5–1.5 | 0.75–1.25 |
| haloprogin 3-iodoprop-2-ynyl 2,4,5-trichlorophenyl ether | 0.25–4.0 | 0.5–1.5 | 0.75–1.25 |

Anesthetic such as lidocaine hydrochloride (acetamide 2-(diethylamino)-N-(2,6-dimethylphenyl) monohydrochloride) and bezocaine (ethyl-p-aminobenzoate) can also be incorporated into the antimicrobial composition. The lidocaine hydrochloride can be present in an amount of from about 0.5–10, preferably 1–7.5, more preferably 2–5, percent by weight of the composition and the benzocaine can be present in an amount of from about 2.5–30 preferably 10–28, more preferably from about 15–25, percent by weight of the antimicrobial composition.

The antimicrobial compositions are preferably prepared with the incorporation of a keratolytic agent, such as allantoin (glyoxyldiureide or 5-ureidohydantoin ($C_9H_6N_4O_3$)). Allantoin can be used in either its base form or as a metal complex, such as, for example, aluminum chlorohydroxyallantoinate and aluminum dihydroxyallantoinate, and as an amino acid complex such as, for example, allantoin N-acetylmethionate complex. Other keratolytic agents useful in the compositions include triacetin, acetic acid, and salicylic acid, which are all strongly acidic, along with polyoxyethylene lauryl ether, and panthenol. Antimicrobial compositions containing benzalkonium chloride are preferably formulated with allantoin since the other keratolytic agents are generally chemically incompatible with the quaternary ammonium compounds. The keratolytic agent is present in the antimicrobial compositions in an amount of about 0.05–5, preferably about 0.25–2.5, and more preferably about 0.5–1, weight percent.

The antimicrobial compositions are prepared with the incorporation of a surfactant that is either a cationic, nonionic, or amphoteric surfactant. The surfactant is preferably chemically compatible within the pH range of about 3–9, where the preferred active agent, benzalkonium chloride, is also stable. Anionic surfactants are not preferred due to their incompatibility with the quaternary ammonium compounds. Various cationic, nonionic, or amphoteric surfactants can be used which are chemically stable in the stated pH range and which are pharmaceutically acceptable and non-toxic. The surfactant, or mixture thereof, is present in an amount of about 0.1–20, preferably 0.5–15, and more preferably about 1–10, weight percent of the antimicrobial composition.

Various surfactants can be employed in the antimicrobial compositions. Examples of nonionic surfactants include, among others, alkanolamide, alkyl dimethylamine oxide, coconut monoethanolamide, cetyl dimethylamine oxide, stearamine oxide, oleamine oxide, and preferably cocoamidopropyl dimethyl amine oxide. Examples of cationic surfactants include, among others, trimethyl cetyl quaternary ammonium chloride, trimethyl coco quaternary ammonium chloride, diquaternary polydimethylsiloxane, and preferably cetyl trimethyl ammonium chloride. Examples of amphoteric surfactants include, among others, cocoamido betaine, oleyl betaine, cocoamphodiacetate, cocamidopropyl hydroxysultaine, and preferably cocoamidopropyl dimethyl betaine.

Individually, it is preferred that the surfactants, if employed, be present in the antimicrobial composition in the following amounts. The amphoteric surfactant can be present in an amount of from amount 0.5–8, preferably about 1–6, and more preferably about 3–5, weight percent; the nonionic surfactant can be present in an amount of from about 0.5–8, preferably 1–6, and more preferably 1.5–5, weight percent; the cationic surfactant can be present in an amount of from about 0.05–5, preferably 0.5–2.5, and more preferably 0.75–1.5, weight percent.

The antimicrobial compositions are aqueous based solutions. Preferably the solvent for the system is freshly distilled water. Deionized water is not preferred as the deionizing resins can result in the presence of pathogens in the deionized water. Further, salts possibly present in deionized water can deactivate quaternary ammonium compounds. The amount of water in the compositions is generally at least about 60, preferably at least about 70, more preferably at least about 80, and even more preferably at least about 85, weight percent.

The antimicrobial compositions can optionally include stabilizers and thickening agents to achieve viscosities within a useful range appropriate for the mode of application. Such agents include hydroxypropyl methylcellulose, hydroxypropyl cellulose, methyl cellulose, carboxy methylcellulose, emulsifying waxes, alkyl triammonium methosulfate, and ceteraryl octanoate.

Although the compositions are aqueous based, certain ingredients may require the presence of a more lipophilic solvent for proper stabilization. Preferred additional solvents are polyhydric alcohol solvents, or "polyol" solvents, such as the polyalkylene glycols having alkylene moieties containing 2–3 carbon atoms, preferably the polyethylene glycols. Molecular weight ranges of from about 200–4000 are preferred for the polyalkylene glycols. These polyol solvents are useful as humectants and emollients and serve to solubilize the paraben compounds.

Other adjuvants such as pH adjustors can be blended with the antimicrobial compositions. Useful pH adjustors can be either organic or non-organic acids or bases, alone or in combination with their respective salts. The most commonly used acidifying agents are, for example, citric acid, sorbic acid, ascorbic acid, malic acid, and succinic acid. The most commonly used basefying agents are, for example, triethanolamine, ammonium hydroxide, potassium hydroxide, and sodium hydroxide. The pH adjustors are used in sufficient quantities to bring the pH of the antimicrobial composition into the desired range, generally from about pH 3 to 9. Other adjuvants can include defoamers, such as dimethicone and dicyclomethicone, emollients, such as oleyl alcohol, oleyl lanolate, and lanolin, moisturizers and humectants, such as vitamin E (alpha tocopherol) in an amount of from about 5,000–15,000 I.U. per ounce of the composition. Also, especially for antimicrobial skin scrubs, abrasives, such as, for example, aluminum and silicon oxides, titanium dioxide, aluminum silicate, and pumice, can be used.

The antimicrobial compositions are preferably prepared with a preservative or mixture thereof. Various preservatives are known in the pharmaceutical industry, and the selected preservative is advantageously selected such that it has antimicrobial activity and thus prevents microbial growth. The more common preservatives are parabens, preferably the methyl and propyl parabens, imidazolidinyl urea, diazolidinyl urea, and the cis isomer of 1-(3-chloroallyl)-3,5,7-triaza-1-azoniaadamantane chloride (CFTA designation, quaternium-15). The amounts of these preservatives to be blended with the antimicrobial compositions are easily determinedby one skilled in the art, however the amount generally is below about 1.5% wt. of the composition.

Although various formulations can be prepared for the stated multiple end uses, preferred ranges for various components used in an antimicrobial composition for treatment of mycotic and bacterial infections of human nails and adjacent tissue, especially for treatment of onychomycosis, onychia, and paronychia, in weight percentages, are set forth in Table 2. The balance of the composition is an aqueous solvent, preferably freshly distilled water.

TABLE 2

| Component | Broad | Preferred | Optimal |
| --- | --- | --- | --- |
| benzalkonium chloride | 0.05–5.0 | 0.10–2.5 | 0.13–2.0 |
| allantoin | 0.05–5.0 | 0.25–2.5 | 0.5–1.0 |
| propylene glycol | 0.00–15.0 | 0.25–12.0 | 0.5–8.0 |
| hydroxypropyl methylcellulose | 0.00–4.0 | 0.25–2.0 | 0.5–1.5 |
| cocoamidopropyl dimethyl betaine | 0.5–8.0 | 1.0–6.0 | 3.0–5.0 |
| cocoamidopropyl dimethyl amine oxide | 0.5–8.0 | 1.0–6.0 | 1.5–3.0 |
| cetyl trimethyl ammonium chloride | 0.0–5.0 | 0.5–2.5 | 0.75–1.5 |
| methyl paraben | 0.01–1.0 | 0.02–0.8 | 0.05–0.25 |
| propyl paraben | 0.01–1.0 | 0.02–0.8 | 0.05–0.25 |
| cis isomer of 1-(3-chloroallyl)-3,5,7-triaza-1-azonia-adamantane chloride | 0.01–1.0 | 0.05–0.5 | 0.1–0.25 |
| diazolinoyl urea | 0.01–1.0 | 0.05–0.5 | 0.1–0.25 |
| triethanolamine | trace | trace | trace |
| citric acid | trace | trace | trace |

The antimicrobial compositions are generally prepared by blending the constituents together until a homogeneous mixture results. If surface treated hydropropyl methyl cellulose is used as a stabilizer, then it is generally blended at the beginning of the preparation in the aqueous solution with the pH of the solution being preferably adjusted to about 8–10 to aid in the dissolution. If nonsurface treated hydropropyl methyl cellulose is used, such as with mouthwash compositions, the temperature of the mixture is adjusted upward during the addition until the stabilizer is dissolved.

A preferred process for preparing an antimicrobial composition, such as those set forth in Table 2 and useful for the treatment of mycotic and bacterial infections of human nails and adjacent tissue, especially for treatment of onychomycosis, onychia, and paronychia, is to dissolve the cis isomer of 1-(3-chloroallyl)-3,5,7-triaza-1-azoniaadamantane chloride (Dowicill 200®, Dow Chemical Co.) into distilled water. Small amounts of hydroxypropyl methyl cellulose are then added and dispersed into the medium. A solution of triethanolamine is then added dropwise to the stirred solution to adjust the pH to about 8–10 to allow the stabilizer to dissolve. An aqueous solution of citric acid is then used to lower the pH below about 7, preferably to about 4.5–6.5. Next, the cocoamidopropyl dimethyl betaine, cocoamidopropyl dimethyl amine oxide, and cetyl trimethyl ammonium chloride are added using mild agitation. The pH is then adjusted to about 6–6.5, as necessary by the dropwise addition of the acidic or basic solutions. The benzalkonium chloride is added with stirring while maintaining the pH at about 6–6.5. The preservatives, the parabens and diazolinoyl urea, and propylene glycol are then added (as a mixture of the preservatives with propylene glycol sold as Germben® II-E, Sutton Laboratories) and mixing is continued until the parabens are dissolved yielding a clear colorless solution. Finally, the allantoin, is added and dissolved to yield a clear colorless solution having a pH of about 6–6.5.

The antimicrobial compositions can be used for various applications all of which are well known in the art. The application route and dosage regimen are dictated by the type of microbial infection to be treated and other variables that are well known by those of skill in the art. As examples of possible applications, the compositions can be used for the treatment of cutaneous and subcutaneous dermatological pathologies of microbially infected mammalian, preferably human, and non-mammalian tissues and their horny keratinized expressions. Examples include administering the compositions to the mammalian skin, hair, scalp, and nails and adjacent tissue. Also, the administration can be to the skin, fur, hooves, claws, and beaks of various mammalian and non-mammalian animals, especially to horses. The composition can be applied as a cleanser, scrub (cleanser with abrasive properties), lotion, or gel.

The antimicrobial compositions can also be used for the treatment of pathologies of microbially infected mammalian, preferably human, and non-mammalian mucous membrane tissues, and for the general cleansing of those same sites. The compositions can be applied in various conventional forms, such as, for example, a vaginal douche, perianal and closotomy wipe, toothpaste, mouthwash, or as an ointment, salve, lotion, gel, paste, etc. As is well known by those of skill in the art, the compositions can be used for treating a multitude of such infections, including, for example, the treatment of oral and genital herpes simplex chancres, thrush, herpes zoster, varicella zoster, tinea barbae, tinea capitis, tinea corporis, tinea cruris, tinea pedis, tinea unguium, tinea versicolor, and acne vulgaris.

The compositions can also be used in a prophylactic manner. For example, the compositions can be used in both a cleanser or a scrub composition for handwashing, for pre-surgical patient skin preparation, as a pre-surgical scrub, for cleansing human skin including the face, foot, arm, leg, groin, and intertriginous areas, etc., and in a composition applied to the inside of gloves, especially in the medical field.

As previously mentioned, the antimicrobial compositions are advantageously utilized in the treatment of onychomycosis. Generally, the treatment is accomplished in the conventional manner by applying the composition to the site of the infection in a sufficient amount to cover the entire afflicted area. The application is made typically 1–3 times daily for a time sufficient to control, and preferably eliminate, the infection.

EXAMPLE

The compositions of the present invention were evaluated in a study of three human patients with fungal infections of the nails. All patients exhibited clinically apparent symptoms of onychomycosis in the form of thick, discolored, crumbly and/or dystrophic nails. Clinical diagnosis of onychomycosis was determined by using a potassium hydroxide preparation test.

The patients were initially graded as to the extent of the infection. A numerical scoring method was developed to measure the degree of nail dystrophy to provide a quantitative measure of the effectiveness of the therapies. FIG. 1 shows the nail 10 divided into five regions. The distal quadrants 20 were assigned a value of 1, the proximal quadrants 30 were assigned a value of 2, and the proximal border 40 was assigned a value of 2. If the region was infected and appeared abnormal (dystrophic), then the numerical value assigned to that region was totaled to provide a nail score. An additional point was added if there was pain associated with the nail and a final point was added if the nail plate was thickened (normal nail plate being less than about 0.5 mm thick). The percentage of the nail involved was also recorded.

The three patients were initially treated twice daily with an antimicrobial composition containing 1.5% wt. benzalkonium chloride as the active ingredient (Composition #1), commercially available as Mycocide NS®. The patients were examined and reevaluated periodically. Limited clinical improvement was observed and the nails were still difficult to debride.

The patients were then treated twice daily with a composition as set forth in Table 3 in weight percent basis, which additionally contains allantoin (Composition #2). The patients were examined and reevaluated periodically. The nails were found to be softer and easier to debride. The cuticle and skin adjacent to the nails were also softer. The nails showed faster clinical improvement in each patient as indicated by the reduced mycotic involvement of the nails as set forth in Tables 4–6.

TABLE 3

| COMPONENT | AMOUNT |
|---|---|
| benzalkonium chloride (BAC)[1] | 1.875 |
| hydroxypropylmethyl cellulose | 1.0 |
| propylene glycol | 0.6 |
| cocoamidopropyl dimethyl betaine | 4.0 |
| cetrimonium chloride | 1.0 |
| quaternium-12[2] | 0.5 |
| quaternium-15 | 0.2 |
| cocoamidopropyl dimethyl amine oxide | 2.0 |
| triethanolamine | trace |
| sodium chloride | trace |
| citric acid | trace |
| diazolidinyl urea | 0.2 |
| methyl paraben | 0.1 |
| propyl paraben | 0.1 |
| allantoin | 0.5 |
| water | Balance |

[1] added as a 50% wt. BAC aqueous solution
[2] CFTA designation for didecyl dioctyl ammonium chloride

TABLE 4

PATIENT #1

| | COMPOSITION #1 | | | | COMPOSITION #2 | | | | |
|---|---|---|---|---|---|---|---|---|---|
| | TIME | | | | | | | | |
| | 0 Weeks | | 8 Weeks | | 17 Weeks | | 23 Weeks | | 29 Weeks | |
| TOE NAIL | SCORE | % | SCORE | % | SCORE | % | SCORE | % | SCORE | % |
| 1 | 10 | 100 | 10 | 100 | 9 | 100 | 7 | 75 | 2 | 40 |
| 2 | 10 | 100 | 10 | 100 | 9 | 100 | 7 | 75 | 2 | 40 |

TABLE 6

PATIENT #3

| | COMPOSITIONS #1 | | NO TREATMENT | | COMPOSITION #2 | | | |
|---|---|---|---|---|---|---|---|---|
| | TIME | | | | | | | |
| TOE NAIL | 0 Weeks | | 40 Weeks | | 61 Weeks | | 76 weeks | |
| | SCORE | % | SCORE | % | SCORE | % | SCORE | % |
| 1 | 6 | 80 | 9 | 100 | 9 | 100 | 8 | 100 |
| 2 | 9 | 100 | 9 | 100 | 9 | 100 | 8 | 100 |
| 3 | 9 | 100 | 9 | 100 | 9 | 100 | 8 | 100 |
| 4 | 9 | 100 | 9 | 100 | 9 | 100 | 8 | 100 |
| 5 | 9 | 100 | 9 | 100 | 9 | 100 | 8 | 100 |
| 6 | 6 | 80 | 8 | 100 | 8 | 100 | 6 | 80 |
| 7 | 7 | 80 | 8 | 100 | 8 | 100 | 8 | 100 |
| 8 | 6 | 80 | 6 | 80 | 8 | 100 | 1 | 20 |
| 9 | 6 | 80 | 8 | 100 | 8 | 100 | 2 | 40 |
| 10 | 9 | 100 | 8 | 100 | 8 | 100 | 2 | 40 |

TABLE 5

PATIENT #2

| | COMPOSITION #1 | | | | COMPOSITION #2 | | | |
|---|---|---|---|---|---|---|---|---|
| | TIME | | | | | | | |
| TOE NAIL | 0 Weeks | | 52 Weeks | | 71 weeks | | 77 Weeks | |
| | SCORE | % | SCORE | % | SCORE | % | SCORE | % |
| 1 | 10 | 100 | 10 | 100 | 4 | 60 | 4 | 50 |
| 2 | 1 | 20 | 1 | 20 | 4 | 60 | 1 | 20 |
| 3 | 9 | 100 | 9 | 100 | 7 | 60 | 2 | 40 |
| 4 | 9 | 100 | 8 | 100 | 2 | 40 | 0 | 0 |
| 5 | 9 | 100 | 9 | 100 | 3 | 60 | 1 | 10 |
| 6 | 10 | 100 | 10 | 100 | 6 | 80 | 4 | 40 |
| 7 | 9 | 100 | 9 | 100 | 2 | 40 | 2 | 10 |
| 8 | 9 | 100 | 9 | 100 | 7 | 80 | 2 | 40 |
| 9 | 1 | 20 | 6 | 80 | 1 | 20 | 0 | 0 |
| 10 | 9 | 100 | 9 | 100 | 9 | 100 | 2 | 40 |

Patient #1 was treated with Composition #1 for 8 weeks. After this initial treatment, the patient reported some pain relief. The treatment with Composition #2 was then initiated and the patient was re-examined after 9, 15, and 21 weeks of that treatment, week totals #17, 23, and 29, respectively. The patient reported no pain by week #23 and clearing was observed at the proximal nail border. By week #29, only distal tip involvement was observed.

Patient #2 was treated with Composition #1 for a year. Composition #2 treatment was then initiated immediately following the one year treatment, and after 19 weeks of treatment with Composition #2 (week #71), the patient reported no pressure pain and diminished nail thickness was observed on 9 toes. Also, at week #71, clearing of the proximal nail border was observed on 9 toes and at the proximal quadrants on 5 toes. At week #77, after 25 weeks of treatment with Composition #2, the level of involvement was significantly reduced.

Patient #3 was treated with Composition #1 for 40 weeks. Treatment was discontinued for a period of 21 weeks. A second therapy, using Composition #2, was then initiated. After 15 weeks of treatment (week #76) all toes showed diminished nail thickness, and clearing was observed on 3 toes at the proximal nail border and proximal quadrants.

What is claimed is:

1. A method for cleansing an animal, comprising administering to the area to be cleansed an antimicrobial composition comprising:

(a) benzalkonium chloride, as an antimicrobial agent, present in an amount of from 0.05–5 weight percent of said antimicrobial composition;

(b) allantoin, present in an amount of about 0.05–5 weight percent of said antimicrobial composition;

(c) about 0.1–20 weight percent surfactant, which is not the same as the antimicrobial agent, comprising at least one nonionic, cationic or amphoteric surfactant; and (d) at least about 60 weight percent water.

2. The method of claim 1 wherein said antimicrobial composition is in the form of a cleanser or scrub.

3. The method of claim 1 wherein said antimicrobial composition is administered to the skin of a human.

4. A method for preventing the onset of a microbial infection, comprising administering to an area to be treated an antimicrobial composition comprising:

(a) benzalkonium chloride, as an antimicrobial agent, present in an amount of from 0.05–5 weight percent of said antimicrobial composition;

(b) allantoin, present in an amount of about 0.05–5 weight percent of said antimicrobial composition;

(c) about 0.1–20 weight percent surfactant, which is not the same as the antimicrobial agent, comprising at least one nonionic, cationic or amphoteric surfactant; and (d) at least about 60 weight percent water.

5. The method of claim 4 wherein said antimicrobial composition is administered to the skin of a human.

6. The method of claim 1 wherein the benzalkonium chloride is percent in an amount of from about 0.1 to about 2.5 weight percent, and the allantoin is present in an amount of from about 0.25 to about 2.5 weight percent, both based on the antimicrobial composition.

7. The method of claim 6 wherein the surfactant comprises an amphoteric surfactant in an amount of from about 0.5 to about 8 weight percent, and a cationic surfactant in an amount of from about 0.05 to about 5 weight percent, of the antimicrobial composition.

8. The method of claim 6 wherein said antimicrobial composition is administered to the skin of a human.

9. The method of claim 4 wherein the benzalkonium chloride is present in an amount of from about 0.1 to about 2.5 weight percent, and the allantoin is present in an amount of from about 0.25 to about 2.5 weight percent, both based on the antimicrobial composition.

10. The method of claim 9 wherein the surfactant comprises an amphoteric surfactant in an amount of from about 0.5 to about 8 weight percent, and a cationic surfactant in an amount of from about 0.05 to about 5 weight percent, of the antimicrobial composition.

11. The method of claim 9 wherein said antimicrobial composition is administered to the skin of a human.

12. A method for cleaning an animal, comprising administering to the area to be cleansed an antimicrobial composition comprising:
 (a) benzalkonium chloride, as an antimicrobial agent, present in an amount of from 0.13–2 weight percent of said antimicrobial composition;
 (b) allantoin, present in an amount of about 00.5–2.5 weight percent of said antimicrobial composition;
 (c) from about 1 to about 6 weight percent of an amphoteric surfactant;
 (d) from about 1 to about 6 weight percent of a non-ionic surfactant;
 (e) from about 0.5 to about 2.5 weight percent of a cationic surfactant;
 (f) from about 0.5 to about 8 weight percent propylene glycol; and
 (g) at least about 60 weight percent water.

13. A method for cleansing an animal, comprising administering to the area to be cleansed an antimicrobial composition comprising:
 (a) at least one antimicrobial agent comprising at least one quaternary ammonium compound present in an amount of from 0.05–5 weight percent of said antimicrobial composition;
 (b) allantoin, present in an amount of about 0.05–5 weight percent of said antimicrobial composition;
 (c) about 0.1–20 weight percent surfactant, which is not the same as the antimicrobial agent, comprising at least one nonionic, cationic or amphoteric surfactant; and
 (d) at least about 60 weight percent water.

14. The method of claim 13 wherein said antimicrobial composition is administered to the skin of a human.

15. The method of claim 13 wherein said surfactant comprises an amphoteric surfactant present in an amount of from about 0.5–8 weight percent of said antimicrobial composition.

16. The method of claim 13 wherein said surfactant comprises a cationic surfactant present in an amount of from about 0.05 to about weight percent of said antimicrobial composition.

17. A method for cleansing an animal, comprising administering to the area to be cleansed an antimicrobial composition consisting essentially of:
 (a) at least one antimicrobial agent comprising at least one quaternary ammonium compound present in an amount of from 0.05–5 weight percent of said antimicrobial composition;
 (b) allantoin, present in an amount of about 0.05–5weight percent of said antimicrobial composition;
 (c) about 0.1–20 weight percent surfactant, which is not the same as the antimicrobial agent, comprising at least one nonionic, cationic or amphoteric surfactant;
 (d) at least one preservative, which is not the same as the antimicrobial agent,
 (e) optionally up to 15 weight percent proplene glycol; and
 (f) at least about 60 weight percent water.

18. A method for preventing the onset of a microbial infection, comprising administering to an area to be treated an antimicrobial composition comprising:
 (a) at least one antimicrobial agent comprising at least one quaternary ammonium compound present in an amount of from 0.05–5 weight percent of said antimicrobial composition;
 (b) allantoin, present in an amount of about 0.05–5 weight percent of said antimicrobial composition;
 (c) about 0.1–20 weight percent surfactant, which is not the same as the antimicrobial agent, comprising at least one nonionic, cationic or amphoteric surfactant; and
 (d) at least about 60 weight percent water.

19. The method of claim 18 wherein said antimicrobial composition is administered to the skin of a human.

20. The method of claim 18 wherein the surfactant comprises an amphoteric surfactant in an amount of from about 0.5 to about 8 weight percent, and a cationic surfactant in an amount of from about 0.05 to about 5 weight percent, of the antimicrobial composition.

21. An aqueous antimicrobial pharmaceutical composition for topical or mucous membrane administration of an antimicrobial agent, consisting essentially of:
 (a) at least one antimicrobial agent comprising at least one quaternary ammonium compound present in a therapeutically effective, non-toxic quantity of from about 0.05 to about 5 weight percent of the antimicrobial composition;
 (b) allantoin, present in an amount of about 0.05–5 weight percent of the antimicrobial composition;
 (c) at least one surfactant, which is not the same as said antimicrobial agent, comprising at least one nonionic, cationic or amphoteric surfactant, said surfactant being present in an amount of 0.1–20 weight percent of the antimicrobial composition;
 (d) a preservative, which is not the same as said antimicrobial agent; and
 (e) at least 80 weight percent water.

22. The antimicrobial composition of claim 21 wherein the water is present in an amount of at least about 85 weight percent.

23. The antimicrobial composition of claim 21 wherein the surfactant comprises a cationic surfactant, said cationic surfactant being present in an amount of from about 0.05 to about 5 weight percent of said antimicrobial composition.

24. The antimicrobial composition of claim 21 wherein the surfactant comprises an amphoteric surfactant, said amphoteric surfactant being present in an amount of from about 0.5 to about 8 weight percent of said antimicrobial composition.

25. The antimicrobial composition of claim 21 further comprising from 0.25–12 weight percent propylene glycol.

26. The antimicrobial composition of claim 21 wherein the quaternary ammonium compound comprises benzalkonium chloride.

27. The antimicrobial composition of claim 26 wherein the benzalkonium chloride is present in an amount of from about 0.10 to about 5 weight percent.

28. The antimicrobial composition of claim 27 wherein the surfactant comprises a cationic surfactant, said cationic surfactant being present in an amount of from about 0.05 to about 5 weight percent of the antimicrobial composition.

29. The antimicrobial composition of claim 27 wherein the surfactant comprises a nonionic surfactant, said nonionic surfactant being present in an amount of from about 0.5 to about 8 weight percent of the antimicrobial composition.

30. The antimicrobial composition of claim 27 wherein the surfactant comprises an amphoteric surfactant, said amphoteric surfactant being present in an amount of from about 0.5 to about 8 weight percent of the antimicrobial composition.

31. The antimicrobial composition of claim 27 wherein the composition is in the form of a cleanser, a scrub, a vaginal douche, a perianal wipe, a colosotomy wipe, a toothpaste, a mouthwash, or a gel.

32. The antimicrobial composition of claim 26 wherein the benzalkonium chloride is present in an amount of from about 0.1 to about 2.5 weight percent, and the allantoin is present in an amount of from about 0.25 to about 2.5 weight percent, both based on the antimicrobial composition.

33. The antimicrobial composition of claim 32 wherein the surfactant comprises an amphoteric surfactant in an amount of from about 0.5 to about 8 weight percent, and a cationic surfactant in an amount of from about 0.05 to about 5 weight percent, of the antimicrobial composition.

34. The antimicrobial composition of claim 33 wherein the surfactant further comprises a nonionic surfactant in an amount of from about 0.5 to about 8 weight percent of the antimicrobial composition.

35. The antimicrobial composition of claim 32 further comprising propylene glycol in an amount up to about 15 weight percent of the antimicrobial composition.

36. The antimicrobial composition of claim 32 further comprising an additional antimicrobial agent selected from the group consisting of tolnaftate, naftifine hydrochloride, terbinafine hydrochloride, ciclopirox olamine, haloprogin, an imidazole, and a triazole.

37. An aqueous antimicrobial pharmaceutical composition for topical or mucous membrane administration of an antimicrobial agent, consisting essentially of:

(a) at least one quaternary ammonium compound comprising benzalkonium chloride in an amount of from 0.1 to 2.5 weight percent of the antimicrobial composition;

(b) allantoin, present in an amount of from about 0.05 to 5 weight percent of the antimicrobial composition;

(c) at least one surfactant comprising at least one nonionic, cationic or amphoteric surfactant, said surfactant being present in an amount of from about 0.1 to 20 weight percent of the antimicrobial composition and which is not the same as the quaternary ammonium compound;

(d) a preservative, which is not the same as the quaternary ammonium compound; and (e) at least 80 weight percent water.

38. The antimicrobial composition of claim 37 wherein the water is present in an amount of at least about 85 weight percent.

39. The antimicrobial composition of claim 37 wherein the benzalkonium chloride is present in an amount of from 0.13 to 2.0 weight percent of the antimicrobial composition.

40. An aqueous antimicrobial pharmaceutical composition for topical or mucous membrane administration of an antimicrobial agent, consisting essentially of:

(a) at least of quaternary ammonium compound comprising benzalkonium chloride in an amount of from 0.1 to 2.5 weight percent of the antimicrobial composition;

(b) allanation, present in an amount of from about 0.05 to 0.5 weight percent of the antimicrobial composition;

(c) at least one surfactant comprising at least one nonionic, cationic or atmospheric surfactant, said surfactant being present in an amount of from about 0.1 to 20 weight percent of the antimicrobial composition and which is not the same as the quaternary ammonium compound;

(d) propylene glycol present in an amount of from about 0.25 to 12.0 weight percent of the antimicrobial composition;

(e) a preservative, which is not the same as the quaternary ammonium compound; and (f) at least 80 weight percent water.

41. The antimicrobial composition of claim 40 wherein the water is present in an amount of at least about 85 weight percent.

42. The antimicrobial composition of claim 40 wherein the benzalkonium chloride is present in an amount of from 0.13 to 2.0 weight percent of the antimicrobial composition.

* * * * *

UNITED STATES PATENT AND TRADEMARK OFFICE
CERTIFICATE OF CORRECTION

PATENT NO. : 5,661,170
DATED : August 26, 1997
INVENTOR(S) : Chodosh

It is certified that error appears in the above-identified patent and that said Letters Patent is hereby corrected as shown below:

Column 3, line 17, delete the word "antimicrobail and insert therefor --antimicrobial--;

Column 5, line 13, delete the word "amount" and insert therefor --about--;
Column 6, line 12, insert a space between the words "determined" and "by";
Column 6, line 42, delete the word "diazolinoyl" and insert therefor --diazolidinyl--;

Column 8, line 62, delete "CFTA" and insert therefor --CTFA--;
Column 9, Table 5 should appear before Table 6;
Column 11, line 24, delete "00.5-2.5" and insert therefor --0.05-2.5--;
Column 11, line 66, insert a space between "0.05-5" and "weight".

Signed and Sealed this

Nineteenth Day of May, 1998

Attest:

BRUCE LEHMAN

Attesting Officer

Commissioner of Patents and Trademarks